(12) United States Patent
D'Arienzo

(10) Patent No.: US 9,448,143 B2
(45) Date of Patent: Sep. 20, 2016

(54) DEVICE FOR REMOVING SAMPLES FROM A MATERIAL FLOW

(71) Applicant: HOLCIM TECHNOLOGY LTD, Rapperswil-Jona (CH)

(72) Inventor: Simone D'Arienzo, Merone-Como (IT)

(73) Assignee: HOLCIM TECHNOLOGY LTD., Rapperswil-Jona (CH)

( * ) Notice: Subject to any disclaimer, the term of this patent is extended or adjusted under 35 U.S.C. 154(b) by 121 days.

(21) Appl. No.: 14/370,404

(22) PCT Filed: Jan. 3, 2013

(86) PCT No.: PCT/IB2013/000007
§ 371 (c)(1),
(2) Date: Jul. 2, 2014

(87) PCT Pub. No.: WO2013/104971
PCT Pub. Date: Jul. 18, 2013

(65) Prior Publication Data
US 2015/0034274 A1    Feb. 5, 2015

(30) Foreign Application Priority Data

Jan. 12, 2012  (AT) .................................. A 31/2012

(51) Int. Cl.
*G01N 1/20* (2006.01)
*F27D 7/02* (2006.01)

(52) U.S. Cl.
CPC ........... *G01N 1/20* (2013.01); *F27D 2007/023* (2013.01)

(58) Field of Classification Search
CPC ....................................................... G01N 1/20
USPC ............. 73/863.52, 863.53, 863.81, 863.51, 73/863.54, 863.57, 863.82
See application file for complete search history.

(56) References Cited

U.S. PATENT DOCUMENTS

| | | | |
|---|---|---|---|
| 1,761,123 A * | 6/1930 | Gruver | F02F 1/183 227/434 |
| 2,370,260 A | 2/1945 | Robinson | |
| 3,802,270 A | 4/1974 | Daniels et al. | |
| 4,625,570 A | 12/1986 | Witherspoon et al. | |
| 5,072,624 A * | 12/1991 | Montgomery | G01N 1/20 73/863.41 |

FOREIGN PATENT DOCUMENTS

| | | |
|---|---|---|
| DE | 10 2009 027 750 A1 | 1/2011 |
| WO | 2011/006869 A1 | 1/2011 |

OTHER PUBLICATIONS

International Search Report dated May 24, 2013, issued in International Application PCT/IB2013/000007.
International Preliminary Examination Report dated May 24, 2013, issued in International Application PCT/IB2013/000007.
International Preliminary Examination Report dated Apr. 29, 2014, issued in International Application PCT/IB2013/000007.

* cited by examiner

*Primary Examiner* — Laura Martin
*Assistant Examiner* — Jean Morello
(74) *Attorney, Agent, or Firm* — Fitch, Even, Tabin & Flannery LLP

(57) ABSTRACT

In a device for taking samples from a material flow of fine-grained and dry material, in particular in the cement industry, comprising an upwardly open sample chamber (2) capable of being introduced into, and retracted from, the material flow through an introduction socket, the sample chamber (2) is formed in a rod-shaped body (1) translationally guided between a sampling position and a retracted position, and the sample chamber (2) has an openable bottom (7).

20 Claims, 3 Drawing Sheets

DEVICE FOR REMOVING SAMPLES FROM A MATERIAL FLOW

CROSS-REFERENCE TO RELATED APPLICATIONS

Figure 1:
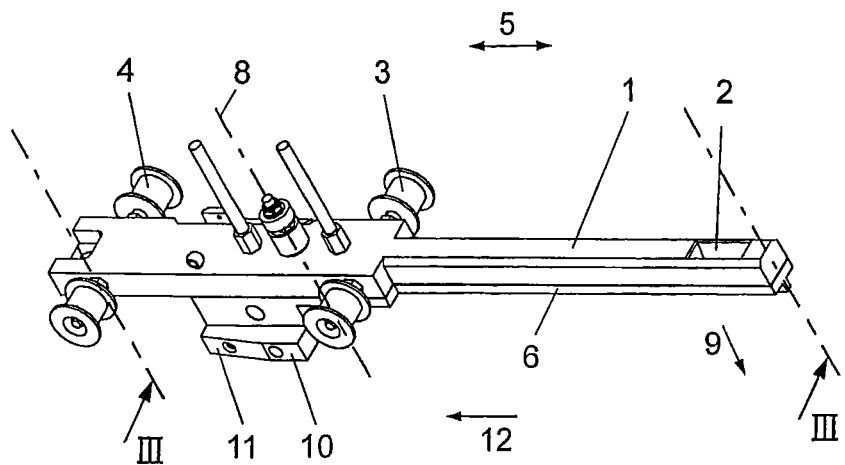

This Application is a U.S. National Stage Application filed under 35 U.S.C. §371 of International Application PCT/IB2013/000007, filed Jan. 3, 2013, designating the United States, which claims priority from Austrian Patent Application A 31/2012, filed Jan. 12, 2012, the complete disclosures of which are hereby incorporated herein by reference in their entirety for all purposes.

The invention relates to a device for taking samples from a material flow of fine-grained and dry material, in particular in the cement industry, comprising an upwardly open sample chamber capable of being introduced into, and retracted from, the material flow through an introduction socket.

The invention further relates to a heat exchanger arrangement of a cement clinker production plant, including a plurality of heat exchangers in which raw meal can be preheated and optionally precalcined in counter-flow to the hot exhaust gases from the clinker kiln, wherein a vertically or obliquely downwardly extending duct of the heat exchanger string, which is provided for a hot-meal flow, comprises an introduction socket through which the sample chamber of the sampling device according to the invention is capable of being brought into the hot-meal flow.

The regular taking of samples from a material flow of an, in particular, hot, fine-grained and dry material above all is of great importance in the cement industry for process control. Thus, it is, for instance, known to take samples of hot meal coming from the raw-meal preheater or precalciner, as is described in the review "Zement-Kalk-Gips", No. 8/1994, pp. 468 et seq. As pointed out there, the necessity of taking samples results from the fact that volatile compounds such as alkalis, sulphur and chlorine, among others, are introduced into the combustion process along with the cement raw materials and fuels. Elevated concentrations of these substances in connection with excessive volatilities and hence resulting salt cycles in the kiln intake and in the lower heat exchanger region frequently cause significant operational and even quality problems. A recognizable sign for emerging process changes is to be found in the salt enrichments in the hot meal of the lowermost cyclone stage of a suspension-type heat exchanger. When exceeding a limit value, which is specific to every kiln installation, interventions or modifications in the process control will be required. The operational difficulties involved, such as the formation of crusts, can normally only be controlled by manual cleaning, regular blasting with air cannons or the occasional ignition of compressed gas cartridges as well as the connection of a gas bypass into the kiln intake region.

The internal salt cycles can be calculated from analyses of the raw-meal and hot-meal samples. From these, the specific salt content is determined according to a specific algorithm. When this salt content exceeds a critical limit value, emerging process disturbances can inter alia be eliminated by reducing the salt content via a gas bypass system. Such a partial withdrawal of hot kiln exhaust gases involves considerable energy and material losses and, therefore, constitutes a correspondingly high cost factor. Consequently, the minimization of bypass quantities is a priority objective of operational efforts.

The taking of hot-meal samples, moreover, serves to determine the degree of calcination of the hot meal. The degree of calcination is an important control parameter in the context of the process control of a clinker production plant.

Sampling devices in the case of hot-meal removal must be designed for use at temperatures up to 1000° C. Furthermore, it is important to cool the taken sample as rapidly as possible in order for the substance state of the sample to change as little as possible, for instance to avoid further calcination of the hot meal. This means that the sample chamber filled with material has to be withdrawn from the material flow as rapidly as possible, followed by an evacuation as rapid as possible.

Another difficulty in taking a sample from a material flow is the control of the sample amount, since the material freely falling merely due to gravity will reach the sampling device in a relatively uncontrolled manner. When taking a sample, it has to be ensured, on the one hand, that the sample is present in a minimum amount allowing for the performance of the respectively desired analysis steps. On the other hand, the removal of too large an amount would be uneconomical.

Besides, there is the risk of an obstruction or blockage of the sampling device, in particular of the channel or introduction socket provided for introducing the sample chamber into the hot material flow. Such obstruction or blockage can, for instance, occur by the material from the material flow collecting in the channel, in the introduction socket or on sampling device components exposed to the material flow, thus possibly leading to major material agglomerations, which may impede or render difficult the unhampered entry of the sample chamber into the material flow.

The present invention, therefore, aims to provide a sampling device by which the above-mentioned problems can be taken into account.

To solve this object, the invention in a device of the initially defined type contemplates that the sample chamber is formed in a rod-shaped body translationally guided between a sampling position and a retracted position, and that the sample chamber has an openable bottom. Sampling is thus performed in a simple manner by pushing the rod-shaped body, in which the sample chamber is integrated, through the introduction socket at least partially into the duct carrying the material flow such that the sample chamber reaches the material flow. The sample chamber is then kept within the material flow for a defined period of time until a desired amount of the fine-grained material has collected in the sample chamber. After this, the rod-shaped body is retracted to such an extent that the sample chamber is removed from the material flow and, through the introduction socket, is brought into a region in which it can be easily and rapidly evacuated. A simple translational oscillating movement of the rod-shaped body will thus do to enable sampling. The structural expenditures will consequently be reduced while ensuring a reliable mode of functioning.

The rod-shaped body at the same time functions to seal the introduction socket in order to prevent the usually very hot fine-grained material from penetrating outwardly through the introduction socket. Sealing will be particularly successful if, as in correspondence with a preferred further development of the invention, the rod-shaped body has a cross section substantially corresponding to the clear cross section of the introduction socket.

Obstructions or blockages can be prevented in that possible material deposits in the interior of the introduction socket are entrained by the oscillating movement of the rod-shaped body and returned into the material flow. To this end, the configuration is preferably devised such that the end face facing the material flow of the rod-shaped body substantially corresponds to the clear cross section of the introduction socket.

The upwardly open sample chamber formed in the rod-shaped body provides a defined volume capable of being filled with material, wherein excess material can drop down over the edge of the sample chamber as soon as the sample chamber is filled to capacity. A material accumulation possibly projecting beyond the edge of the sample chamber will be stripped off, preferably on the mouth of the introduction socket, during the retraction of the rod-shaped body such that the maximum sample amount is actually limited by the volume of the sample chamber.

After or during the retraction of the rod-shaped body, the sample chamber is evacuated by opening the bottom of the chamber. An evacuation of the chamber is possible through the openable bottom even without requiring a separate manipulation of the rod-shaped body in its entirety, e.g. by tilting or turning. The evacuation will thereby be substantially more rapid and efficient. The openable bottom is preferably formed by a body displaceable in the bottom plane. The displaceable body is, for instance, comprised of a rod-shaped bottom-forming body that may be substantially flatter than the rod-shaped body accommodating the sample chamber, yet preferably has the same width. The body accommodating the sample chamber and the body forming the bottom thus together form a rod-shaped overall body having a rectangular cross section. The rectangular cross section enables a translational guidance as play-free and reliable as possible of the body within the introduction socket or an introduction channel.

The bottom-forming body can be displaced in the bottom plane in various ways in order to open the sample chamber. It is, for instance, conceivable to retract the bottom body in the direction of the translational movement relative to the rod-shaped body accommodating the sample chamber. The configuration, however, is advantageously devised such that the bottom-forming body is pivotably mounted on the rod-shaped body so as to allow for a scissor-like opening movement of the bottom.

In order to be able to automatically open the bottom possibly without time delay after the retraction or even during the retraction of the sample chamber from the material flow, it is preferably provided that a control element, in particular a control ramp, of the body forming the bottom cooperates with a stationary overrun element to control the opening movement of the bottom as a function of the displacement stroke of the rod-shaped body.

The evacuation of the sample chamber in this case can be facilitated in that, as in correspondence with a preferred further development, the rod-shaped body cooperates with a stationary stop acting in the direction of displacement and defining the retracted position of the rod-shaped body. Striking against the stationary stop causes a jerky stoppage of the rod-shaped body, whereby the thus created impact will act on the material contained in the sample chamber and cause the detachment of the material from the chamber walls so as to subsequently enable the material to fall down from the opened chamber under the action of gravity. In this respect, it is particularly advantageous if the sudden stoppage of the rod-shaped body occurs at a moment at which the bottom of the sample chamber is already opened. A preferred further development in this respect provides that the control element is arranged in such a manner that the opening movement of the bottom is terminated when the rod-shaped body comes to lie on the stationary stop.

The material falling down from the sample chamber reaches a collecting container, which is subsequently transported to a lab for performing the desired analyses. A preferred configuration in this respect contemplates that a sample collecting container is arranged below the sample chamber in the retracted position, wherein a free falling path for the material falling from the sample chamber is provided between the bottom of the sample chamber and the sample collecting container. The free fall of the material is of particular relevance for ensuring a sufficiently rapid cooling of the sample. Tests have shown that over a falling path of merely 40 to 50 cm the material will cool from 900° C. to a sufficiently low temperature to prevent further calcination.

Certain materials involve the risk of the material adhering to the walls of the sample chamber or tending to form bridges in the interior of the sample chamber, which would lead to problems during the evacuation of the sample chamber. These problems can be overcome in that, as in correspondence with a further preferred configuration, the sample chamber widens towards the bottom. The lower region of the sample chamber will consequently contain more material than the upper region, wherein the higher weight of the material contained in the lower region after having opened the bottom will entrain the material contained in the upper region, thus destroying possible bridges. The sample chamber preferably widens conically, which with a sample chamber having a rectangular ground section will lead to the sample chamber having a trapezoidal cross section.

A further measure to promote the complete evacuation of the sample chamber preferably resides in that the rod-shaped body is in operative connection with a vibration device, e.g. an ultrasonic probe. The vibration device is preferably directly fastened to the rod-shaped body, making the latter oscillate.

The adherence of material in the sample chamber is preferably also prevented in that the inner surface of the sample chamber is surface-treated, in particular smoothed, in order to avoid adherences.

In that the retraction of the rod-shaped body accommodating the sample chamber and the subsequent evacuation of the sample chamber can be performed very rapidly owing to their design, the expenditures involved in the cooling of the sampling device where necessary are minimized, wherein a separate cooling device may even be renounced entirely. This will be favored even further if the rod-shaped body and the bottom-forming body are made of metal, in particular steel, according to a preferred further development. A particularly sturdy configuration hardly prone to wear is provided in that the rod-shaped body is advantageously designed as a solid metal body.

The translational displacement of the rod-shaped body between the sampling position and the retracted position is preferably performed in that the rod-shaped body cooperates with a hydraulic or pneumatic drive. Such a drive is characterized by a high reliability even at the high temperatures prevailing in the sampling region, thus allowing a fully automatic operation of the device.

In order to ensure the precise guidance of the rod-shaped body, a further preferred configuration contemplates that the rod-shaped body is translationally guided on at least one guide rail. The rod-shaped body advantageously carries at least two rollers cooperating with the guide rail.

The sampling device according to the invention is particularly suitable for taking hot-meal samples from a heat exchanger in a cement clinker production plant. According to a further aspect, the invention, therefore, also relates to a heat exchanger arrangement of a cement clinker production plant, including a plurality of heat exchangers in which raw meal can be preheated and optionally precalcined in counterflow to the hot exhaust gases from the clinker kiln, wherein a vertical or obliquely downwardly extending duct of the heat exchanger string, which is provided for a hot-meal flow, comprises an introduction socket, said heat exchanger arrangement comprising a sampling device according to the invention, whose sample chamber is capable of being introduced into the hot-meal flow through the introduction socket.

In a preferred manner, the axis of the introduction socket encloses an angle of 0° to 20°, in particular 0° to 10°, with the horizontal. The rod-shaped body accommodating the sample chamber is consequently introduced into the material flow in a horizontal or approximately horizontal direction such that the material of the material flow, which is usually oriented vertically or approximately vertically, can be efficiently collected in the sample chamber. The described arrangement allows for the removal of the sampling device during running operation without hot material penetrating from the introduction socket. Maintenance options are thus improved, and the risk of accidents and injuries is thereby reduced.

The introduction socket is preferably arranged on a hot-meal outlet conduit of the lowermost suspension-type heat exchanger stage of the heat exchanger string.

Figure 2:
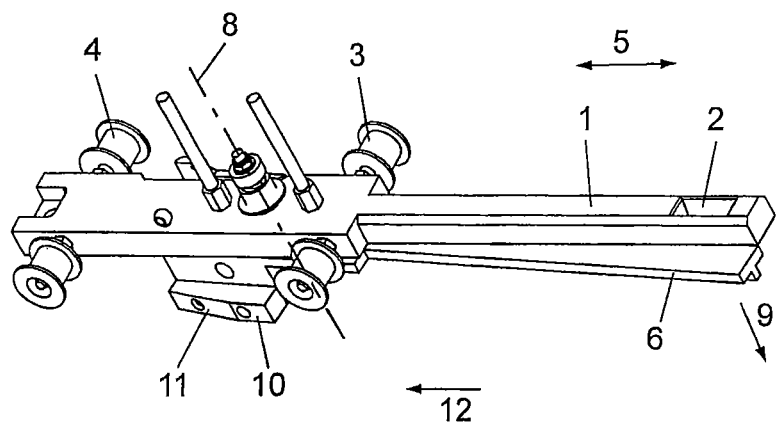
Figure 3:
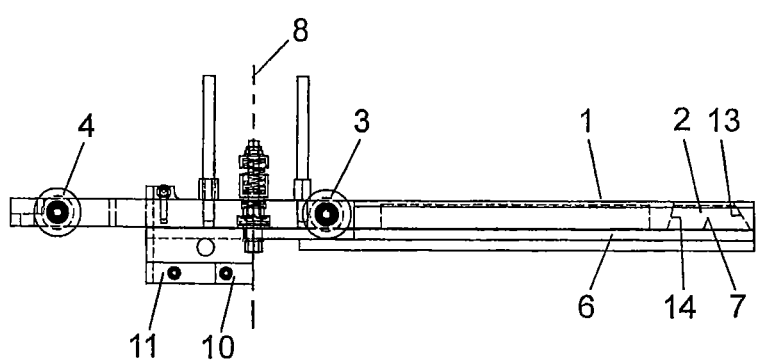
Figure 4:
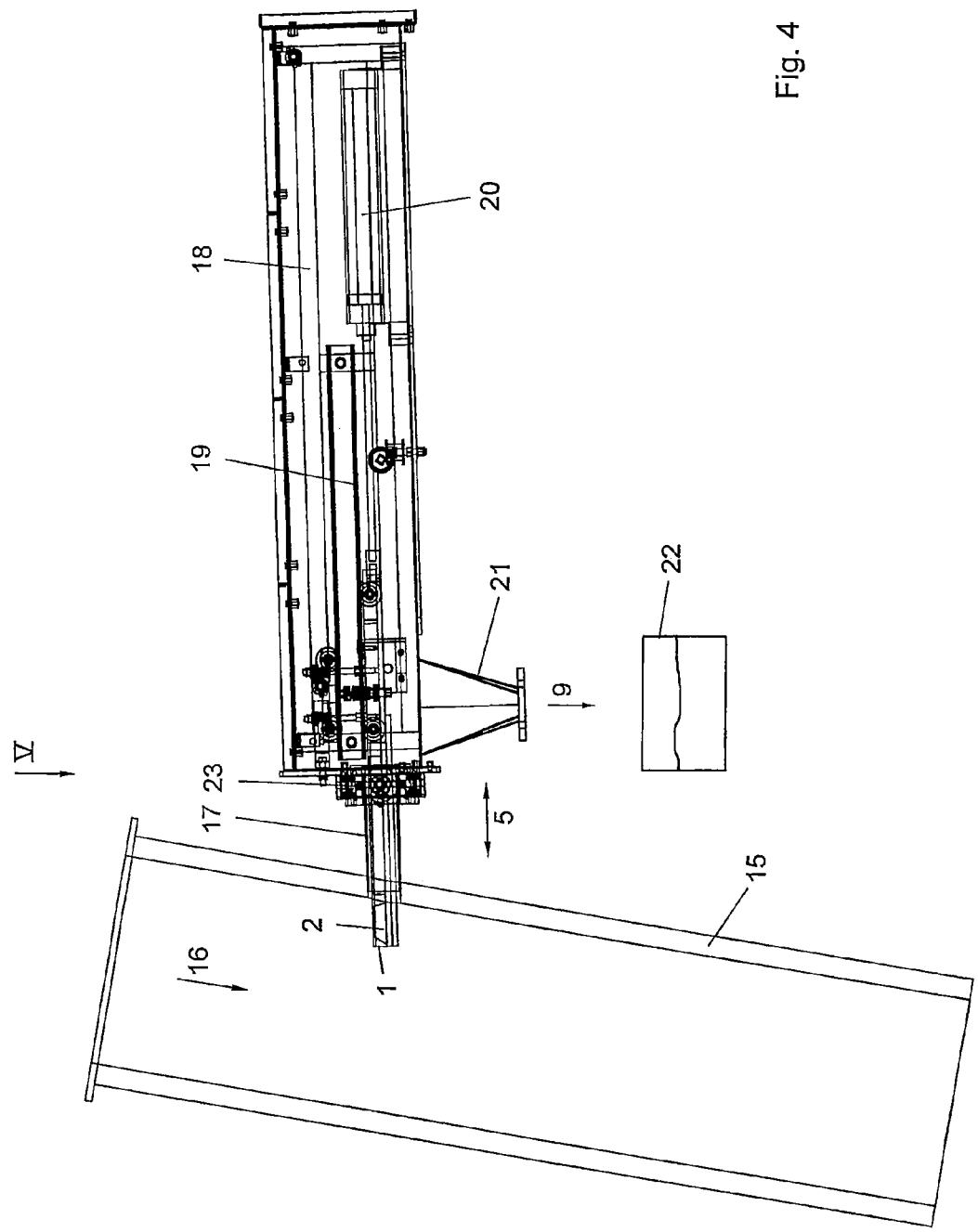
Figure 5:
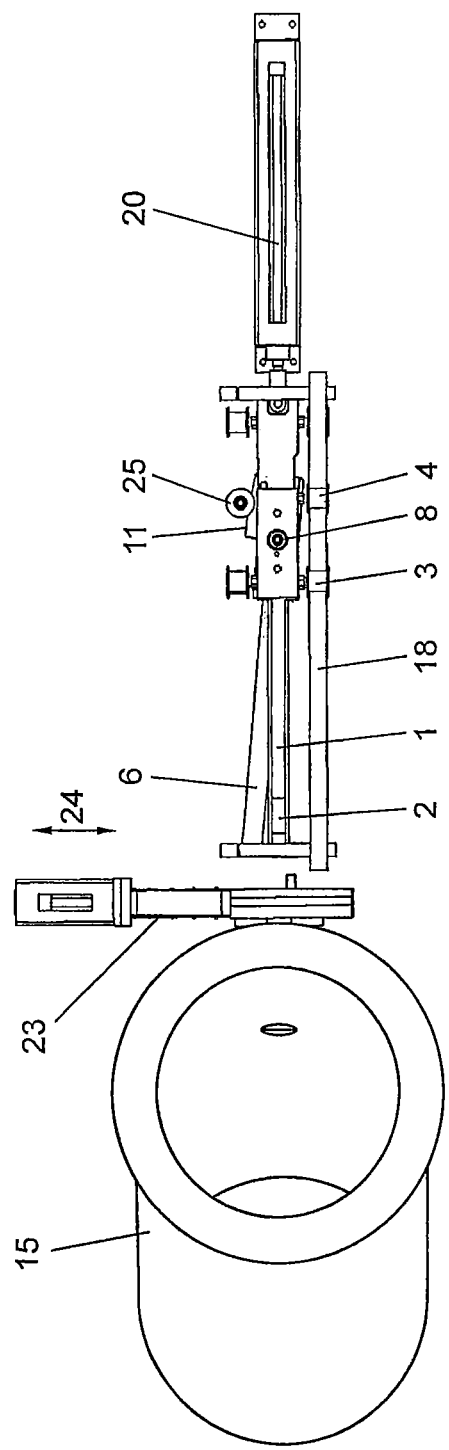

In the following, the invention will be explained in more detail by way of an exemplary embodiment schematically illustrated in the drawing. Therein, FIG. 1 is a perspective view of a sampling device according to the invention; FIG. 2 shows the device according to FIG. 1 with the bottom of the sample chamber opened; FIG. 3 depicts a longitudinal section along line of FIG. 1; FIG. 4 illustrates the installation situation of the device on a hot-meal outlet conduit of the lowermost suspension-type heat exchanger stage of a raw-meal preheater for cement clinker production; and FIG. 5 is a view in the sense of arrow V of FIG. 4.

In FIG. 1, a rod-shaped body having a substantially rectangular cross section is denoted by 1. In its front region, the rod-shaped body 1, which is made of solid material, comprises an aperture forming an upwardly open sample chamber 2. The sample chamber 2 provides a defined volume for fine-grained material to be collected from a material flow. In the rear region, the rod-shaped body 1 is widened and carries two roller pairs 3 and 4, which are each freely rotatably mounted and able to roll over stationary guide rails (not illustrated) in order to translationally guide the rod-shaped body 1 in the sense of double arrow 5.

From FIG. 1, a bottom-forming body 6 is, moreover, apparent, which is congruent with the rod-shaped body 1 at least in the front region of the device. The bottom-forming body 6, in its front region, thus has the same width as the rod-shaped body 1, yet is substantially flatter. In the position illustrated in FIG. 1, the bottom-forming body 6 forms the bottom 7 of the sample chamber 2. In its rear region, the bottom-forming, body 6 is mounted on the rod-shaped body 1 so as to be pivotable about a pivot axis 8 and can be pivoted from the position illustrated in FIG. 1 into the position illustrated in FIG. 2. In doing so, the bottom-forming body 6 performs a scissor-like movement relative to the rod-shaped body 1, thus opening, or pivoting aside, the bottom 7 of the sample chamber 2 so as to allow the material present in the sample chamber 1 to fall out in the sense of arrow 9 under the action of gravity.

The flat bottom-forming body 6 has a rectangular cross section comprising a rib extending in the direction of displacement (double arrow 5), which rib ensures sufficient mechanical strength of the flat bottom-forming body 6.

In its rear region, the flat bottom-forming body 6 comprises a laterally projecting mechanical control element 10 including a ramp 11 located behind the pivot axis 8. When retracting the device in the sense of arrow 12, the ramp 11 runs onto a stationary overrun element, which is not illustrated for the sake of clarity, and causes pivoting of the rod-shaped body as lifting proceeds.

From the sectional illustration according to FIG. 3, it is apparent that the sample chamber 2 comprises a bottom 7 formed by the bottom-forming body 6. The front wall 13 and the rear wall 14 of the sample chamber 2 diverge downwardly such that a trapezoidal cross section results. The sample chamber 2 thus widens downwardly.

FIGS. 4 and 5 illustrate how the sampling device can be arranged on a hot-meal outlet conduit of a raw-meal preheater. The hot-meal duct, in which hot meal (not illustrated) flows in the direction of arrow 16, is denoted by 15. The duct 15 comprises an introduction socket 17, which passes through the wall of the duct 15 and opens into the interior of the duct 15. For taking a hot-meal sample, the rod-shaped body 1 of the sampling device is pushed into the interior of the duct 15 through the introduction socket 17 until the sample chamber 2 is completely arranged in the interior of the duct 15 as illustrated in FIG. 4. The sampling device is fastened to a carrying structure 18 carrying, among others, the guide rails 19 on which the rod-shaped body 1 is translationally guided by the aid of the roller pairs 3 and 4. The carrying structure 18, moreover, accommodates a hydraulic, pneumatic or electric drive, e.g. formed by a hydraulic cylinder piston unit 20, to move the rod-shaped body 1 between the sampling position illustrated in FIG. 4 and the retracted position indicated in FIG. 5.

In the retracted position, the sample chamber 2 reaches a drain funnel 21, which is also arranged on the carrying structure 18 and via which the hot-meal sample, which drops down under the action of gravity after having opened the bottom of the sample chamber 2, reaches the sample collecting container 22.

From the top view according to FIG. 5, in which the carrying structure and one of the two guide rails 19 have been omitted for the sake of clarity, it is apparent that the introduction socket 17 can be closed by a gate valve 23 displaceable in the sense of double arrow 24, when the rod-shaped body 1 of the sampling device is in the retracted position. Furthermore, the mechanism for automatically opening the sample chamber bottom can be seen. Said mechanism comprises a stationary overrun roller 25, which is fastened to the carrying structure 18 and onto which the control ramp 11 formed on the laterally pivotable body 6 constituting the bottom 7 of the sample chamber 2 runs. The overrunning of the control ramp 11 causes a force acting substantially perpendicularly to the direction of displacement 5 to be exerted on the bottom-forming body 6, effecting the scissor-like pivoting-out of the bottom-forming body 6 as the displacement movement of the rod-shaped body 1 proceeds.

The invention claimed is:

1. A device for taking samples from a material flow of fine-grained and dry material comprising an upwardly open sample chamber (2) capable of being introduced into, and retracted from, the material flow through an introduction socket, which sample chamber (2) is formed in a rod-shaped body (1) translationally guided between a sampling position and a retracted position and has an openable bottom, wherein the openable bottom is formed by a bottom-forming body (6) displaceable in the bottom plane, which is preferably movable together with the rod-shaped body (1) between the sampling position and the retracted position, a control element (10), of the bottom-forming body (6) forming a bottom (7) cooperates with a stationary overrun element to control an opening movement of the bottom in an opening direction as a function of a displacement stroke of the rod-shaped body (1), wherein the control element (10) is arranged in such a manner that the opening movement of the bottom is terminated when the rod-shaped body (1) comes to lie on a stationary stop.

2. A device according to claim 1, wherein the bottom-forming body (6) is pivotably mounted on the rod-shaped body (1) so as to allow for a scissor-like opening movement of the bottom (7).

3. A device according to claim 1, wherein the rod-shaped body (1) and the bottom-forming body (6) are made of metal.

4. A device according to claim 1, wherein the rod-shaped body (1) is designed as a solid metal body.

5. A device according to claim 1, wherein the rod-shaped body (1) has an end face facing the material flow and substantially corresponding to a clear cross section of the introduction socket.

6. A device according to claim 1, wherein the rod-shaped body (1) cooperates with the stationary stop acting in the opening direction (12) and defining the retracted position of the rod-shaped body (1).

7. A device according to claim 1, wherein a sample collecting container is arranged below the sample chamber (2) in the retracted position, wherein a free falling path for the material falling from the sample chamber (2) is provided between the bottom (7) of the sample chamber (2) and the sample collecting container.

8. A device according to claim 1, wherein the sample chamber (2) widens towards the bottom (7) or has a trapezoidal shape that widens towards the bottom.

9. A device according to claim 1, wherein the rod-shaped body (1) is in operative connection with a vibration device.

10. A device according to claim 1, wherein an inner surface of the sample chamber (2) is surface-treated in order to avoid adherences.

11. A device according to claim 1, wherein the rod-shaped body (1) cooperates with a hydraulic, pneumatic or electric drive.

12. A device according to claim 1, wherein the control element (10) is formed as a control ramp (11).

13. A device according to claim 1, wherein the inner surface of the sample chamber (2) is smoothed in order to avoid adherences.

14. A device according to claim 1, wherein the rod-shaped body (1) is translationally guided on at least one guide rail.

15. A device according to claim 14, wherein the rod-shaped body (1) carries at least two rollers (3, 4) cooperating with the guide rail.

16. A heat exchanger arrangement of a cement clinker production plant, including a plurality of heat exchangers in which raw meal can be preheated and optionally precalcined in counter-flow to the hot exhaust gases from a clinker kiln in the cement clinker production plant, wherein the heat exchanger arrangement comprises a string of heat exchangers, a vertical or obliquely downwardly extending duct of the heat exchanger string, which is provided for a hot-meal flow, the duct comprising an introduction socket, and a sampling device according to claim 1 whose sample chamber is capable of being introduced into the hot-meal flow through the introduction socket.

17. A heat exchanger arrangement according to claim 16, wherein an axis of the introduction socket encloses an angle of 0° to 20° with the horizontal.

18. A heat exchanger arrangement according to claim 16, wherein an axis of the introduction socket encloses an angle of 0° to 10° with respect to the horizontal.

19. A heat exchanger arrangement according to claim 16, wherein the heat exchanger string has a lowermost suspension-type heat exchanger stage with a hot-meal outlet conduit and the introduction socket is arranged on the hot meal conduit.

20. A device for taking samples from a material flow of fine-grained and dry material comprising
   a rod-shaped body (1) translationally guided between a sampling position and a retracted position, said rod-shaped body (1) having a bottom surface,
   an upwardly open sample chamber (2) capable of being introduced into, and retracted from, the material flow through an introduction socket, said sample chamber (2) formed in said rod-shaped body (1) so as to be translationally guided between the sampling position and the retracted position, said sample chamber (2) having an openable bottom in the bottom surface of said rod-shaped body (1),
   a bottom-forming body (6) having a flat surface opposing the bottom surface of said rod-shaped body (1), said bottom-forming body (6) displaceable in the bottom plane and movable together with said rod-shaped body (1) between the sampling position and the retracted position, wherein said bottom-forming body (6) is laterally pivotably mounted on said first rod-shaped body (1) so as to allow for a lateral scissor-like opening and closing movement of the flat surface of said bottom-forming body (6) relative to the bottom surface of said rod-shaped body (1) whereby said openable bottom of said sample chamber (2) can be opened and closed, and
   a control element (10) of said bottom-forming body (6) forming a bottom (7) cooperates with a stationary overrun element to control an opening movement of said bottom-forming body (6) in an opening direction as a function of a displacement stroke of said rod-shaped body (1), wherein the control element (10) is arranged in such a manner that the opening movement of said bottom-forming body (6) is terminated when said rod-shaped body (1) comes to lie on a stationary stop.

* * * * *